United States Patent [19]

Hilberath et al.

[11] 4,109,701
[45] Aug. 29, 1978

[54] METHOD OF CONVEYING HEAT ENERGY

[75] Inventors: Friedrich Hilberath, Walberberg; Johannes Teggers, Wesseling, both of Fed. Rep. of Germany

[73] Assignee: Rheinische Braunkohlenwerke AG., Cologne, Fed. Rep. of Germany

[21] Appl. No.: 601,214

[22] Filed: Aug. 1, 1975

[30] Foreign Application Priority Data

Aug. 7, 1974 [DE] Fed. Rep. of Germany ....... 2437975

[51] Int. Cl.² ........................... F28C 3/02; C09K 5/00
[52] U.S. Cl. ............................................ 165/1; 60/649; 165/2; 165/61; 165/64; 252/188.3 R; 260/449 M
[58] Field of Search ........................ 252/188.3 R, 373; 260/449 M; 237/81; 60/649; 165/1, 2, 58, 61, 64, 105

[56] References Cited

U.S. PATENT DOCUMENTS

| | | | |
|---|---|---|---|
| 3,128,163 | 4/1964 | Weittenhiller et al. ......... | 260/449 M |
| 3,690,550 | 9/1972 | Hilberath et al. ............... | 260/449 M |
| 3,958,625 | 5/1976 | Wentorf .................... | 165/2 |
| 3,971,634 | 7/1976 | Ranken et al. ................. | 260/449 M |

*Primary Examiner*—Benjamin R. Padgett
*Assistant Examiner*—Irwin Gluck
*Attorney, Agent, or Firm*—Connolly and Hutz

[57] ABSTRACT

Disclosed is an improvement in the process of conveying heat energy by means of the exothermic and endothermic reactions involved in the conversion and re-forming of methane. According to the invention, methane is steam-reformed in an endothermic reaction, utilizing heat energy, to a gas comprising hydrogen, carbon monoxide, carbon dioxide and water vapor. The gas is substantially freed of water and is conveyed to a location wherein heat energy is desired. The heat energy is released upon re-forming methane and the exothermic reaction wherein methane is re-formed is carried out at elevated pressure and at least in part at temperatures between about 400° and 650° C. The methane so produced can be recycled if desired.

3 Claims, 1 Drawing Figure

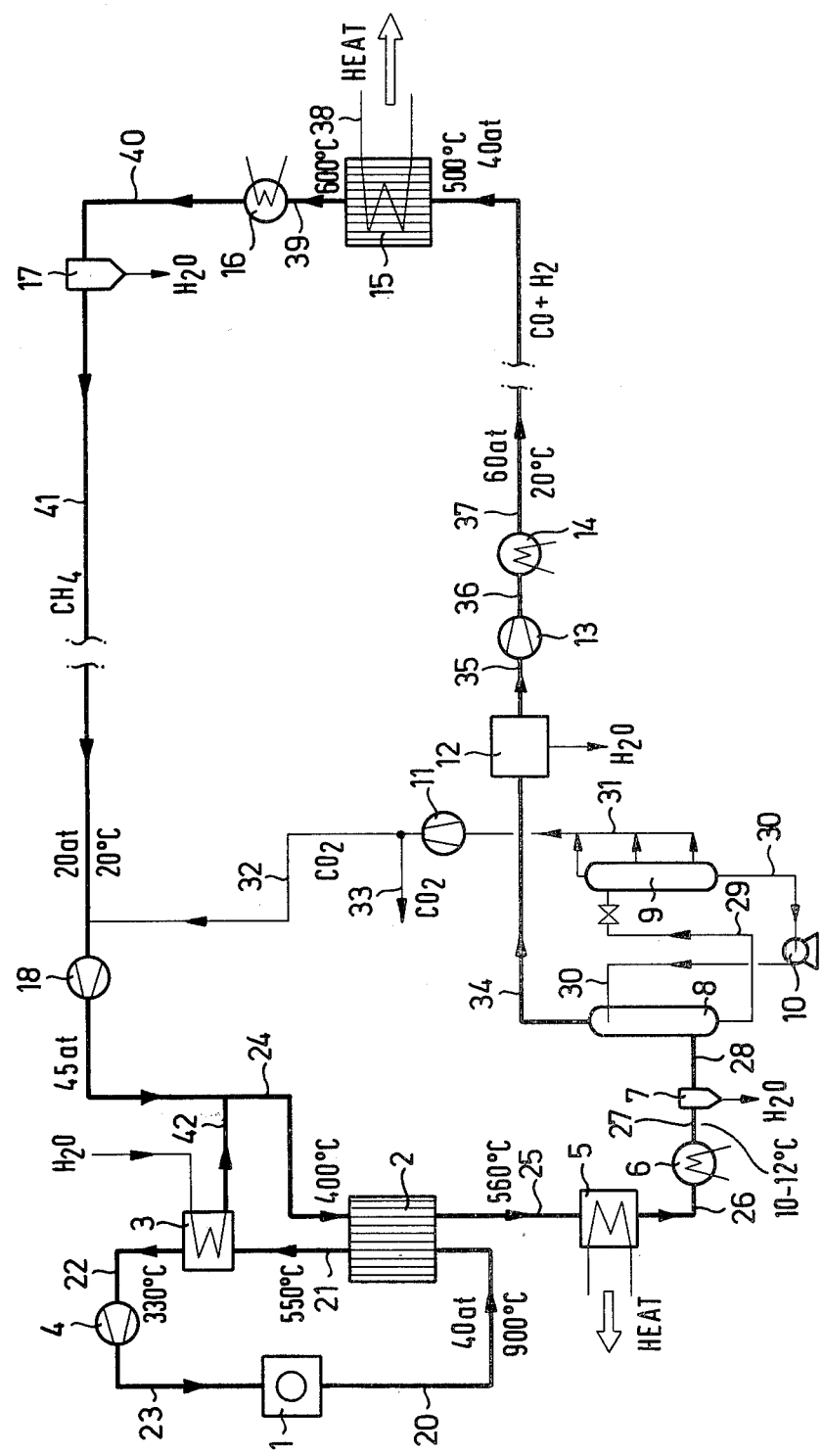

METHOD OF CONVEYING HEAT ENERGY

BACKGROUND OF THE INVENTION

Generally, heat energy is converted into electric energy, which then is transmitted to the location of energy consumption. This, however, is accompanied by considerable energy losses.

It has therefore been suggested to cleave a suitable chemical compound in an endothermic reaction, utilizing energy cheaply available at the location of separation. The reaction products so produced are conveyed to the desired location of heat consumption, there to form again the chemical compound in an exothermic chemical reaction. The heat energy released thereby is utilized, and then the compound may be recycled to the location of the separating reaction.

Suitable compounds suggested for such reactions are, for example, metal hydrides which may be cleaved with heat into hydrogen and liquid metal. After the conveyance of these products to the desired location of heat consumption, which is not possible economically over great distances because the metal is in fused state, a recombination of the metal hydride is accomplished, heat is obtained and it is utilized in the desired manner (See U.S. Pat. No. 3,075,361 for details of such process).

A considerable improvement in the combination of endothermic and exothermic reaction sequences was accomplished by using for this purpose the conversion of methane to a mixture of carbon monoxide, water vapor, carbon dioxide and hydrogen and the re-formation of methane from these constituents in an exothermic methanization reaction (See German Pat. No. 1,298,233 for details of such process). In this manner, only gases need be conveyed from the endothermic reaction site to the exothermic reaction site, so that even very great distances between the places of heat production and heat consumption could be bridged economically.

SUMMARY OF THE INVENTION

It has been found in accord with this invention that this process of conveying heat by
(a) applying heat energy for the catalytic steam-reforming of methane,
(b) conveying the cooled gases obtained thereby to the desired place of energy consumption,
(c) catalytically reacting the gases to again form methane while utilizing the heat released thereby, and optionally,
(d) recycling the re-formed methane back to the steam-reforming unit may be improved and carried out unexpectedly effectively.

In accordance with the present invention the above reaction sequence is carried out in such a manner that water is substantially completely removed from the gas obtained from the steam-reforming of methane, carbon dioxide present in the said gas is partially or wholly separated and the subsequent catalytic reaction to form methane (methanization reaction) is carried out under elevated pressure of between 10 – 100 atmospheres gauge and at least partially at temperatures of between about 400° – 650° C. By maintaining these conditions, it becomes unexpectedly possible to carry out the entire process considerably more economically, despite the increased use of apparatus, and to increase the heat utilization generally by about 10% or more as compared to a procedure which includes the presence of water vapor in customary amounts.

DETAILED DESCRIPTION OF THE INVENTION

The steam-reforming of methane into reformed gas is carried out in the known manner with the addition of water vapor at about 400°–900° C, optionally at elevated pressures, e.g. up to 100 atmospheres gauge, generally utilizing catalysts containing approximately 3–75, prefered 6 – 60% wt. nickel on carriers of heat-resistant material such as the oxides of aluminium, magnesium, silicon, zirconium, copper, chromium and others. Mixtures of these oxides can also be used. The carriers may— for instance — be impregnated by a solution of a nickel-salt, e.g. nickelcarbonate or nickelnitrate, and then be calcined at temperatures of approximately 300° – 700° C or more. It is also possible to calcine the carrier before impregnation. Binding agents, for instance low melting cement may be added to the carriers to increase their strength. These agents should however be inert. Catalysts frequently contain an alkali or earth-alkali. For example, the hydroxides of potassium or calcium or the corresponding carbonates may be added during manufacture. Such contents of alkali or earth alkali may be up to 10% wt. The catalysts can be formed in the usual manner, for instance in pills or rings. These steam-reforming processes are well known in the literature and any suitable method known in the art may be utilized. The resulting gas which generally comprises hydrogen, carbon monoxide, carbon dioxide, water vapor, and optionally also methane is freed of water vapor and water in a known manner to such an extent that the water vapor content in the gas obtained is not more and preferably less than that which exists for the gas at normal pressure and ambient temperature. In accordance with the temperature this means for example at 20° C not more than about 20 g/m$^3$, at 40° C not more than about 50 g/m$^3$ water vapor in the gas mixture. This may be accomplished, for example, by cooling the separation gas to the ambient temperature or preferably lower, e.g. in the case of an ambient temperature of 20° to 18° C or lower, say down to 5° C, and condensation of the water vapor. In addition, the residual moisture still present in the gas may be entirely or partially removed, e.g. with the aid of molecular sieves.

Normally some carbon dioxide will be removed with the water and, if desired, further carbon dioxide may be removed from the separation gas, e.g. by a washing step, known per se, such as a water wash carried out under elevated pressure or a wash with other solvents, e.g. N-methylpyrollidone, propylene carbonate, or at low temperatures, at or below 0° C, with methanol.

In this connection, it sometimes will be advantageous to retain only small portions, e.g. less than 12%, of carbon dioxide in the separation gas. Generally, the content of carbon dioxide in the gas mixture introduced into the methanization step should be in the range of about 1 to 15% and may not exceed about 25% by volume. The carbon dioxide separated from the re-formed gas may be entirely or partially recycled into the steam-reforming unit until the desired equilibrium has been set. Due to this step, as a further advantage, a reduction of the problems of corrosion in the conveyance of the dried gas through pipe lines is achieved.

In the methanization step, the reaction of carbon monoxide or carbon dioxide with hydrogen is carried out at least partially at temperatures of between about 350° – 750° C. A temperatue range of about 400° – 700° C, and particularly of 450° – 650° C, has ben shown to be advantageous. To the extent that there is no desire for a high temperature level for the heat energy being released, the lower temperature range of 350° – 450° C is also utilized.

The dry methanization step carried out according to the invention at the said high temperatures of course requires the use of catalysts suitable therefor. While the dry methanization, particularly as a supplemental step for raising the methane proportions in the gas to above 95%, for example, may be carried out at about 200° – 300° C without difficulties with a number of known catalysts, with a dry methanization at the said higher temperatures, the catalyst to be used must be carefully selected from the possibilities known to one skilled in the art in order that excessive difficulties do not set in, e.g. in view of sooting or formation of carbonaceous deposits and the consequent too rapid decrease in catalyst activity. For example, nickel catalysts, produced under suitable conditions, may be utilized, generally lower nickel contents, e.g. up to 20%, appearing to be preferable. Such catalysts may be manufactured on principle in about the same manner as described for the catalysts used in the steam-reforming of methane. The dry methanization may also be carried out even at higher temperatures, e.g. up to about 850° C, if suitable catalysts are used. For the completion of the reaction of the carbon oxides to methane subsequent to the high-temperature methanization, there may be carried out in a known manner a post-methanization at a lower temperature level, e.g. at 200°– 350° C; here, too, proceeding gradually and drawing off the heat a the respective various temperature levels. The methanization is suitably carried out under elevated pressure, say at 10° – 100 atmospheres gauge, and particularly 20 – 50 atmospheres gauge. It may be suitable, if desired, to recycle a portion of the methane-containing gas into the methanization step in order to guarantee the desired reaction temperature. It may be equally suitable to remove entirely or partially the carbon dioxide contained in the gas. The methane obtained in such a manner is conducted again to the steam-reforming equipment at an elevated pressue through a pipe line. Of course, in this equipment there may also be used entirely or partially methane from another source, e.g. in the form of natural gas. In this instance, the methane originating from the methanization step may be supplied for any other purposes desired, e.g. for combustion and consequently further heat energy utilization or even for chemical conversions. The apparatus and conduits used may be of the customary type and may be operated under the customary conditions.

An example of a suitable procedure for the novel hat energy conveyance of this invention is illustrated schematically in the FIGURE. A suitable agent at high temperature, e.g. helium used as a cooling agent in a high temperature nuclear reactor, at about 900° C coming from a nuclear reactor 1 at a pressure of about 40 atmospheres, is conducted into steam-reforming unit 2 through conduit 20 wherein its heat is utilized for the conversion of methane in the presence of water vapor, optionally also of $CO_2$. The helium leaves the reforming unit at about 550° C through conduit 21, is utilized in the heat exchanger 3 for the evaporation of water and then is returned to nuclear reactor 1 through conduits 22 and 23 with intermediate compression in compressor 4. A mixture of methane, water vapor and $CO_2$ is introduced into steam-reforming unit 2 through conduit 24 about 400° C. The gas mixture obtained leaves the unit through conduit 25 at about 560° C after the catalytic reforming. The gas comprises $H_2O$, CO, $CO_2$, $H_2$ and $CH_4$ and it is cooled by coolers 5 and 6 connected by conduit 26 to about 10° – 12° C; the water condensed out during cooling is separated in separator 7 connected to cooler 6 by conduit 27. The gas, now dried, is conveyed through conduit 28 to washing column 8, wherein the $CO_2$ is substantially completely washed out of the gas. The washing solution is regenerated in column 9 and recycled with the help of pump 10 and conduits 29 and 30 into washing column 8. The $CO_2$ is removed from column 9 by conduit 31 and it is then compressed to the required pressure in compressor 11 and partially supplied to reforming plant 2 by conduits 32 and 24 and partially removed from the process by conduit 33. The remaining gas is conducted via conduit 34 to molecular sieves 12 wherein residual moisture is removed. The gas is then conducted by way of conduits 35, 36 and 37, and compressor 13 and cooler 14 at ambient temperature and at an initial pressure of 60 atmospheres gauge to methanization plant 15 at the desired place of the heat consumption.

It is understood that methanization plant 15 may be located at a considerable distance from unit 2.

The gas enters unit 15 at about 40 atmospheres gauge. Here there occurs the catalytic methanization or reforming of methane at about 500° – 600° C with the removal of the heat released thereby through a suitable means such as a heat exchanging apparatus 38. The gas leaving methanization plant 15 through conduit 39 is cooled in cooler 16. Water condensed during cooling is separated in separator 17 connected to cooler 16 by conduit 40. The gas is then conducted by means of pipe conduit 41, mixed with $CO_2$ coming from conduit 32 and passes to a compressor 18 wherein it is compressed to 45 atmospheres gauge. The compressed gas is conveyed through conduit 24 to plant 2 with intermediate addition of water vapor formed in heat exchanger 3 by means of conduit 42. At this pressure, it is introduced into the steam-reforming unit 2.

What we claim is:

1. In the method of conveying heat energy from a location of heat production to a location of heat consumption wherein methane is endothermically reacted in the presence of water vapor at elevated temperature and pressure at a location of heat production to a gaseous mixture comprising carbon monoxide, water, carbon dioxide, hydrogen, and methane, the gaseous mixture is conveyed to a location of heat consumption, the gaseous mixture is exothermically reacted to re-form methane and the heat energy generated thereby is utilized, the improvement comprising:

after production of said gaseous mixture and before the gaseous mixture is conveyed to a location of heat consumption, removing carbon dioxide from the gaseous mixture, freeing the gaseous mixture of water vapor and water to an extent that the water vapor content in the mixture is not more than that which would exist at normal pressure and ambient temperature;

conveying the so-treated gaseous mixture to a location of heat consumption; and utilizing the so-treated gaseous mixture for the exothermic re-formation of methane in a dry methanization step without steam addition at elevated pressures of between 10 and 100 atmospheres gauge and at temperatures of between about 400° and 650° C.

2. The method according to claim 1 wherein the gaseous mixture is freed of water vapor and water to such an extent that the water vapor content in the mixture is less than that which would exist at normal pressure and ambient temperature.

3. The method according to claim 1 wherein methane reformed in the exothermic methanization step is recycled to the endothermic reaction step.

* * * * *